United States Patent [19]

Merrill

[11] Patent Number: 5,275,838
[45] Date of Patent: Jan. 4, 1994

[54] IMMOBILIZED POLYETHYLENE OXIDE STAR MOLECULES FOR BIOAPPLICATIONS

[75] Inventor: Edward W. Merrill, Belmont, Mass.

[73] Assignee: Massachusetts Institute of Technology, Cambridge, Mass.

[21] Appl. No.: 898,928

[22] Filed: Jun. 12, 1992

Related U.S. Application Data

[63] Continuation-in-part of Ser. No. 486,153, Feb. 28, 1990, Pat. No. 5,171,264.

[51] Int. Cl.$^5$ ............................................. G02C 7/04
[52] U.S. Cl. ........................................ 427/2; 525/937; 523/106
[58] Field of Search .................... 427/2; 351/160; 525/937; 523/106; 530/413; 435/261

[56] References Cited

U.S. PATENT DOCUMENTS

| | | | |
|---|---|---|---|
| 4,152,283 | 5/1979 | Cordrey et al. | 351/160 H |
| 4,280,923 | 7/1981 | Small et al. | 252/323 |
| 4,280,970 | 7/1981 | Kesting | 351/160 H |
| 4,452,892 | 6/1984 | Rosevear | 435/176 |
| 4,687,814 | 8/1987 | Chaumont et al. | 525/242 |
| 4,840,851 | 6/1989 | Golander et al. | 428/523 |
| 4,857,615 | 8/1989 | Bronn et al. | 525/271 |
| 5,019,100 | 5/1991 | Hennink et al. | 351/160 H |
| 5,039,769 | 8/1991 | Molock et al. | 523/106 |
| 5,070,166 | 12/1991 | Su et al. | 351/160 H |
| 5,179,174 | 1/1993 | Elton | 525/937 |

FOREIGN PATENT DOCUMENTS

| | | |
|---|---|---|
| 0068509 | 1/1983 | European Pat. Off. . |
| 0263184 | 4/1988 | European Pat. Off. . |
| 0332261 | 9/1989 | European Pat. Off. . |

OTHER PUBLICATIONS

Rempp, R. & P. Lutz, *Abstracts of the Papers of the American chemical Society* 196:27-Poly (1988).
Rempp, P. et al., *Advances in Polymer Science* 86:145-173 (1988).
Taromi, F. A. and P. Rempp, *Makromol. Chem.* 190:1791-1798 (1989).
Gnanou, Y. et al., *Makromol. Chem.* 189:2885-2892 (1988).
Lutz, P. and P. Rempp, *Makromol. Chem.* 189:1051-1060 (1988).
Rempp, P. et al., *American Chemical Society, Polymer Division Symposium*, Boston, Mass. Apr. 1990.
Merrill, E. W. et al., The 16th Annual Meeting of the Society for Biomaterials, Charleston, S.C., May 20-23, 1990.
Tay, S. W. et al., *Biomaterials* 10:11-15 (1989).

*Primary Examiner*—Shrive Beck
*Assistant Examiner*—Erma Cameron
*Attorney, Agent, or Firm*—Hamilton, Brook, Smith & Reynolds

[57] ABSTRACT

A method for immobilizing polyethylene oxide (PEO) star molecules in the form of hydrogel layers and a product thereof are disclosed. The PEO star molecules are biocompatible and demonstrate non-thrombogenic properties. As such, the PEO star molecule layers have numerous biomedical applications, such as on contact lenses. The hydrogel layers contain a high percentage of terminal hydroxyl groups for attachment of affinity ligands and can be used for separating and purifying therapeutic proteins.

20 Claims, 4 Drawing Sheets

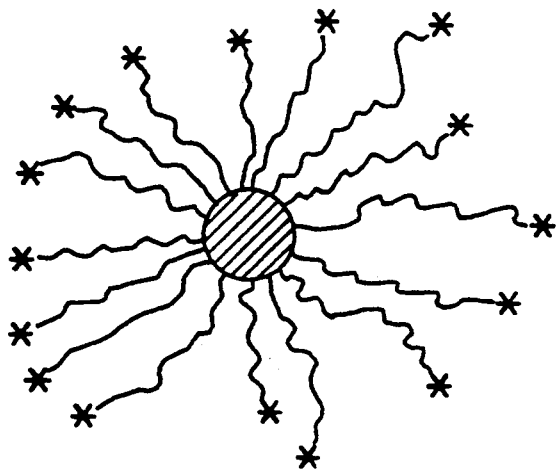
FIG. IA
LEGEND FOR FIG. IA & IB
◯ = CROSS-LINKED DIVINYL BENZENE CORE
∿ = PEO CHAIN
✷ = HYDROXYL GROUP
— = PS CHAIN
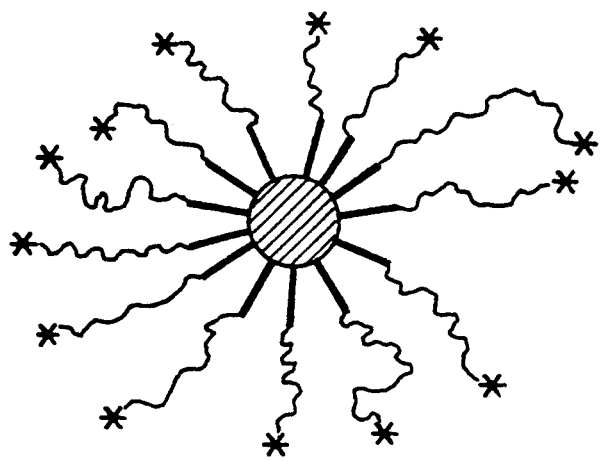
FIG. IB \* = ACTIVATED HYDROXYL, E.G. BY TRESYLATION
▨ = ATTACHMENT TO AMINO GROUP ON SUPPORT SURFACE

IMMOBILIZED POLYETHYLENE OXIDE STAR MOLECULES FOR BIOAPPLICATIONS

RELATED APPLICATION

This application is a continuation-in-part of U.S. patent application Ser. No. 07/486,153 filed Feb. 28, 1990, which issued as U.S. Pat. No. 5,171,264 on Dec. 15, 1992 the teachings of which are incorporated herein by reference.

BACKGROUND OF THE INVENTION

Polyethylene oxide (PEO) is an important biomaterial because it is non-adsorptive toward biopolymers, and is non-thrombogenic, i.e, it does not adsorb proteins of the intrinsic clotting system nor of the platelet membrane. However, when PEO is combined with other molecules at the surface, thrombogenicity may be enhanced. Okkema, *J. Biomat. Sci.* 1:43–62 (1989). Thus, it is essential that no other molecular entity besides PEO be accessible to proteins. It has been widely studied as a blood-contacting biomaterial in various forms: in segmented polyurethanes, in block copolymers with styrene or siloxane blocks, end-linked into junctions through isocyanate reactions, as side-chains on acrylate polymers and as hydrogels cross-linked from PEO solutions.

PEO is naturally soluble in water and certain organic solvents. Therefore, in order to render PEO insoluble it must be cross-linked, or end-linked to a support. The manner in which this is accomplished often affects physical and chemical properties of PEO.

Chemical cross-linking of PEO can be employed, but the chemical cross-linking agent (e.g., a polyfunctional isocyanate) may be incorporated into the PEO. If exposed at the ultimate surface, such a chemical moiety can cause adverse biopolymer reactions, including non-specific binding of proteins and platelet adhesion.

Physically cross-linked PEO produced from polyethylene oxide-polystyrene multiblock polymers or from polyether-urethanes suffers from the presence of the non-PEO materials at the surface. Adverse biological reactions caused by the non-PEO material may often be avoided if the molecular weight of the PEO is made higher than about 5,000. However, such material tends to swell excessively in water and is fragile.

End-linking PEO to supports by various means, so as to leave an available hydroxyl groups for attachment of an affinity ligand, for example, is not easily carried out if the molecular weight of the PEO is more than about 1,000. Furthermore, complete coverage of a surface by end-linking PEO is very difficult, unless the molecular weight is relatively high (several thousand).

Various forms of PEO have also been widely used as a molecular leash for affinity ligands and enzymes. Golander et al., *Int. Chem. Congress of Pacific Basin Societies*, Abstract No. 253, Honolulu, Hi., Dec. 17–22, 1989, Harris, *J. Macromolecular Sci.* C25:325–373 (1985); Holmberg, *Int. Chem. Congress of Pacific Basin Societies*, Abstract No. 255, Honolulu, Hi., Dec. 17–22, 1989. Typically, PEO has terminal hydroxyl groups which can be activated for attachment to biopolymers. Most processes for forming PEO biomaterials, however, reduce the hydroxyl content to very low values or zero. In order to produce a cross-linked PEO having a significant concentration of terminal hydroxyls, low molecular weight PEO (2,000 to 10,000) are required but often result in fragile materials. Alternatively, using short PEO side chains on macromonomers like polyethylene glycol methacrylate may result in exposure of the methacrylate residues at the surface, and these short PEO side chains are almost invariably methyl terminated, so that no hydroxyl exists for subsequent attachment of ligands.

Thus, a need exists for a method of immobilizing PEO to a support surface without detracting from its physical properties and biological compatibility. In addition, it would be desirable to provide a material having a high concentration of hydroxyl groups for attachment to biopolymers.

SUMMARY OF THE INVENTION

This invention pertains to a method for covalently immobilizing polyethylene oxide star molecules onto a support surface and to layers produced by the method. The PEO star molecules are immobilized on the support surface in the form of layers using ionizing radiation, or hydroxyl group activation followed by chemical coupling. The resulting PEO layers have a high concentration of terminal hydroxyl groups which are available for attachment to biospecific affinity ligands. Thus fitted with ligands, the immobilized PEO star molecules can be used as a tool for separating and purifying biological molecules, while greatly reducing or eliminating non-specific binding.

The PEO star molecule layers also have non-thrombogenic properties which make them suitable for applications in which blood contact is required. They are highly biocompatible and have excellent mechanical durability for numerous biomedical applications, including intravenous catheters and implantable vascular prostheses. The layers of this invention can be formed on contact lens materials providing highly hydrophilic protein-resistant surfaces.

BRIEF DESCRIPTION OF THE DRAWINGS

FIG. 1a shows a Type I PEO star molecule having a divinyl benzene (DVB) core and PEO chains attached thereto.

FIG. 1b shows a Type II PEO star molecule having a DVB core and PEO chains attached thereto by polystyrene (PS) chains.

DETAILED DESCRIPTION OF THE INVENTION

Figure 2:
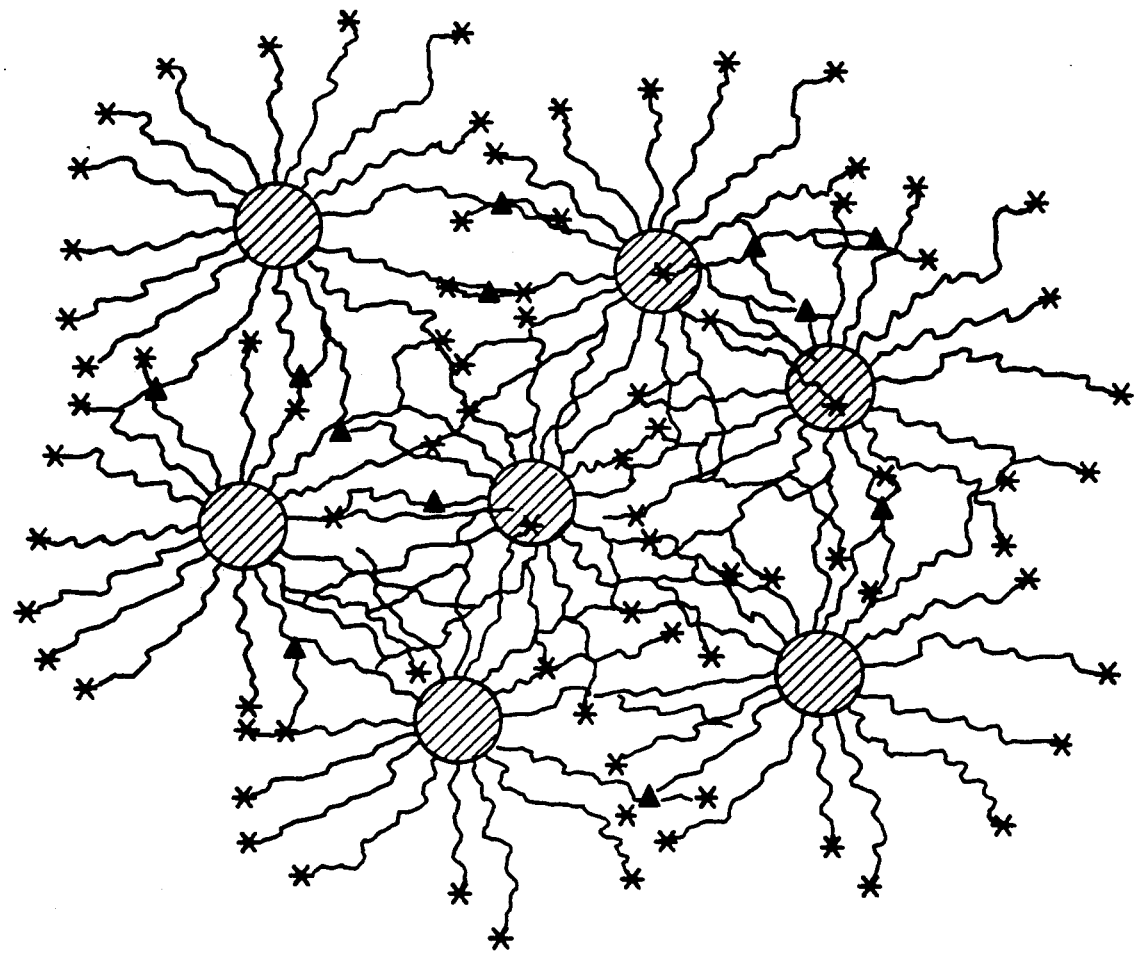
FIG. 2 shows overlapping PEO star molecules (Type I) which are cross-linked to each other by electron irradiation.

Polyethylene oxide star macromolecules have been previously described by Lutz et al., *Makromol. Chemie* 189:1051 (1988) and Gnanou et al., *Makromol. Chemie* 189:2893–97 (1988), the teachings of which are incorporated by reference herein. The star molecules are synthesized by anionic polymerization from divinyl benzene (DVB), ethylene oxide and optionally styrene. They have a core of divinyl benzene (typically on the order of about 50 angstroms) from which a predetermined number of polyethylene oxide chains or "arms" are grown. Generally, the DVB core represents about two weight percent or less of the total star molecule weight. The cores however can be of polymeric material other than divinyl benzene. The length of each PEO chain or arm corresponds to molecular weight and typically ranges from about 1,000 to about 10,000 atomic mass units (a.m.u.). Preferably, each star molecule will have from about six to about 200 arms. The total molecular weight of the star, which is approximately the product of the molecular weight of each arm and the total number of arms, ranges from about $10^5$ to about $10^6$ a.m.u. Two variations of PEO star molecules are shown in FIGS. 1A and 1B and are described herein as Type I and Type II, respectively. Type I star molecules contain a plurality of hydroxy-terminated PEO chains (hydrophilic) that are attached to a hydrophobic DVB core by non-hydrolyzable carbon-carbon bonds. Type II PEO star molecules are of similar composition except that the PEO chains are attached to the DVB core via hydrophobic polystyrene (PS) chains.

The concentration of hydroxy-termini on the PEO arms can be determined in advance by selection of the gross concentration of star molecules and the number of arms carried by the molecule. For example, a star molecule of 100,000 molecular weight with twenty PEO arms has twenty hydroxyl groups. To obtain comparable hydroxyl concentrations with linear PEO polymers, the molecular weight would have to be lowered to 10,000.

The PEO star molecules can be immobilized on a support surface of any geometry (e.g., particles, porous plastic cores, thin plastic film, biomedical device, contact lenses) using ionizing radiation. According to the method, PEO star molecules are dissolved or suspended in an aqueous solution (preferably water) in a concentration sufficient to provide enough star molecules to cover the support surface to a desired thickness. Typically, a sufficient concentration will be around 5 to 15 wt/vol %. Type I star molecules form optically clear homogeneous solutions in water, while Type II star molecules form faintly turbid to opaque suspensions, due to the presence of polystyrene. The resulting solution is then deposited onto the support surface, such as by spraying, spreading, rotating the support or centrifugation.

The star molecules in solution are then cross-linked together and to the surface by exposing them to electron beam radiation which creates free radicals on the arms at random positions, and on the surface. Random coupling then results in the formation of a layer. If the solvent is water, the resulting layer is a hydrogel layer. The term "hydrogel" refers to a broad class of polymeric materials which are swollen extensively in water but which do not dissolve in water. Typically, the solution is exposed to electron radiation in the range of between about one to about ten megarads, most preferably four megarads. Gamma radiation can be used as the radiation source but may result in the degradation of the star molecules unless oxygen is scrupulously excluded. Cross-linking via free radical coupling occurs randomly between segments of the PEO arms, thus allowing the terminal hydroxyl groups to remain available for subsequent activation, such as for coupling affinity ligands to the PEO arms.

FIG. 2 shows several Type I PEO star molecules cross-linked together by electron radiation. The resulting hydrogel layers are of variable thickness but are typically on the order of magnitude of greater than 1 $\mu$M. The thickness of the hydrogel layer can be regulated by various techniques, such as doctor-blade spreading on a support web or centrifugal casting in tubes.

An advantage of electron radiation cross-linking is that the cross-linking reaction proceeds very rapidly, at a rate of approximately one foot per second in the case of web coating. Under a nitrogen blanket, the reaction proceeds by free-radical coupling to produce an essentially pure product without uptake of oxygen. As such, the cross-linking reaction does not alter the chemical composition of the star molecules. Other known cross-linking techniques tend to introduce chemical components which may subsequently affect its biocompatibility. Further, the hydrogel layer presents a surface for contacting biological materials (e.g., blood) which is essentially hydrated PEO chains. As such, the DVB and PS components are inaccessible or not recognizable to these biological molecules.

The resulting hydrogels have significantly greater mechanical strength than hydrogels formed from ordinary linear PEO having the same range of molecular weight as the star (i.e., 100,000 to 300,000). A gel made from 10 wt. % of 100,000 molecular weight linear PEO under identical dosage would have two to ten times lower tensile strength than the network formed from star molecules, and would have only one tenth the number of hydroxyl groups per unit area of surface. The concentrations of hydroxyl ends obtained by stars would translate to linear polyethylene oxide of about 5,000 a.m.u. or less. Such low molecular weight polymers cannot be cross-linked at all, or form gels of low strength with considerable soluble fraction.

In another embodiment, the star molecules can be covalently immobilized to a support surface by tresylation of the terminal hydroxyl groups. The support surface and star molecules are each pretreated prior to immobilization. As such, the support surface should contain active functional groups for immobilizing tresylated star molecules thereto, such as amino and/or thiol groups. Likewise, the star molecules should be tresylated in an appropriate solvent prior to contacting with the support surface. Tresylation is particularly convenient since the PEO is solvated by media appropriate to tresyl chloride (e.g., dichloromethane, chloroform). This method results in a monolayer coating of the hydrogel over the support surface.

According to this method, an organic solvent, such as dichloromethane, comprising PEO star molecules is exposed to tresyl chloride, under conditions to affix the tresyl groups to hydroxy-termini on the star molecules. The resulting tresylated PEO star molecules are then precipitated and recovered, ultimately as a dry active product. Just prior to use, the tresylated PEO star molecules are dissolved in an aqueous solution at a pH of ten or above, so as to favor reaction with amino and/or thiol groups already present on the support surface. The pH-adjusted solution is contacted with a support surface that contains amino and/or thiol groups, under conditions whereby the star molecules become covalently bound in a dense layer to the support surface.

Figure 3:
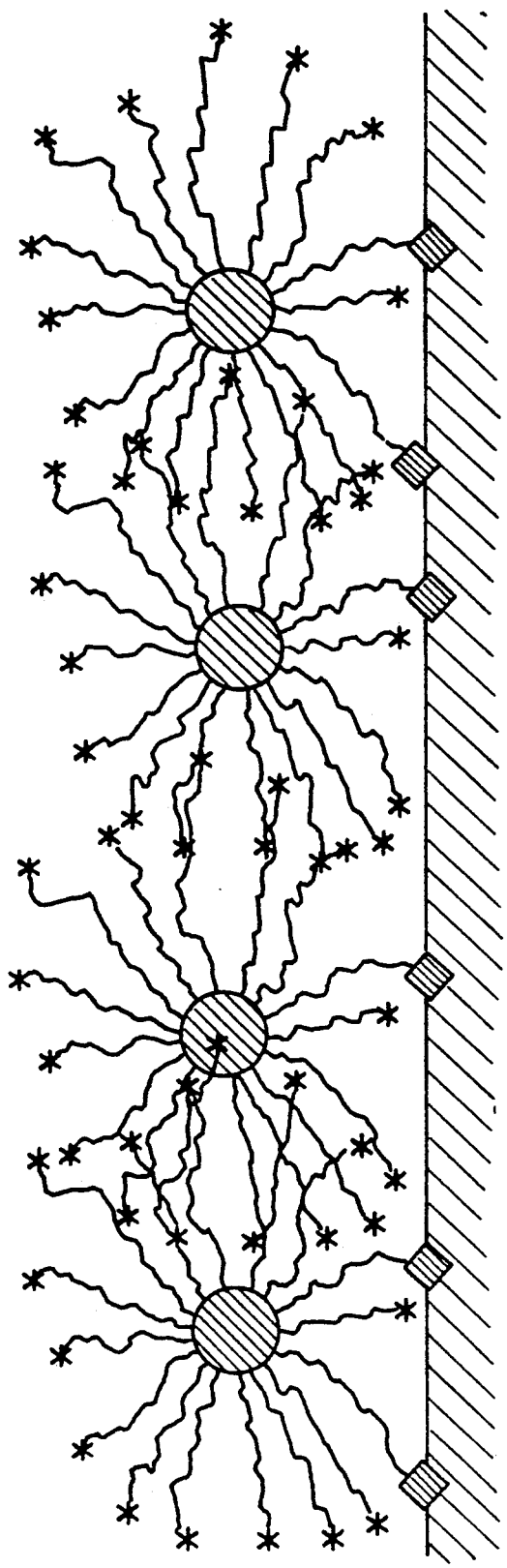
FIG. 3 shows several PEO star molecules (Type I) covalently attached to a support surface by tresylated hydroxyl groups.

This process is further described below by way of illustration. For example, a Cellophane TM (cellulose containing plasticizers) containing support is placed in a bath of tetrahydrofuran and tresyl chloride. The hydroxyl groups on the surface of the Cellophane TM support are then tresylated. Once tresylated, the Cellophane TM support is aminated in a water solution of ethylene diamine (pH 10) which results in binding the group —HN—CH₂CH₂NH₂ to the activated hydroxyl groups. Unreacted diamine is removed by washing with tetrahydrofuran. Likewise, star molecules are tresylated, purified, and then placed into an aqueous buffer (pH 10) containing the aminated Cellophane ™ support. After a period of approximately one hour, the Cellophane ™ support is removed from the solution and rinsed to wash off any unbound star molecules. The star molecules become bound to the amino group via the tresylated hydroxyls. FIG. 3 shows several PEO star molecules immobilized on a support surface. The attachment results from the reaction of amino groups on the support surface with tresylated hydroxyls on the star molecules.

In addition to tresyl chloride, other reagents can be used to react with the terminal hydroxyl groups on the PEO chains. These reagents include tosyl chloride (p-toluene sulfonyl chloride), mesyl chloride (methane sulfonyl chloride), epichlorhydrin, cyanuric chloride (C₃N₃Cl₃), carbonyl diimidazole (CDI) and a mixture of succinic anhydride and succinimide. These reactions are generally described by Harris, "Laboratory Synthesis of Polyethylene Glycol Derivatives," *J. Macromolecular Sci. Reviews in Macro. Chem. Phys.*, C25(3), 325–373 (1985). For example, the hydroxy-terminated polyethylene oxide is reacted with tosyl chloride or mesyl chloride to form a tosylated or mesylated star molecule, respectively. In each case the activated PEO arms can be reacted with any molecule containing an amino or thiol group. By-products liberated by the reaction of the amino or thiol containing compound with the activated PEO arms include tresyl, mesyl or tosyl sulfonic acid, HCl (reaction of cyanuric chloride), imidazole (reaction of CDI), or N-hydroxylsuccinimide (reaction of succinic anhydride and succinimide). There is no by-product liberated in the epichlorhydrin reaction. Among the surface activation chemistries described above, tresylation is the most efficient method in terms of speed and product recovery. Any molecule containing an amino or thiol group, for example a protein, can now become covalently attached to a tresylated, tosylated, or mesylated polyethylene oxide chain by the formation of the very stable —NC— or —SC— bond with the elimination of the respective sulfonic acid: tresyl, tosyl or mesyl.

Figure 4:
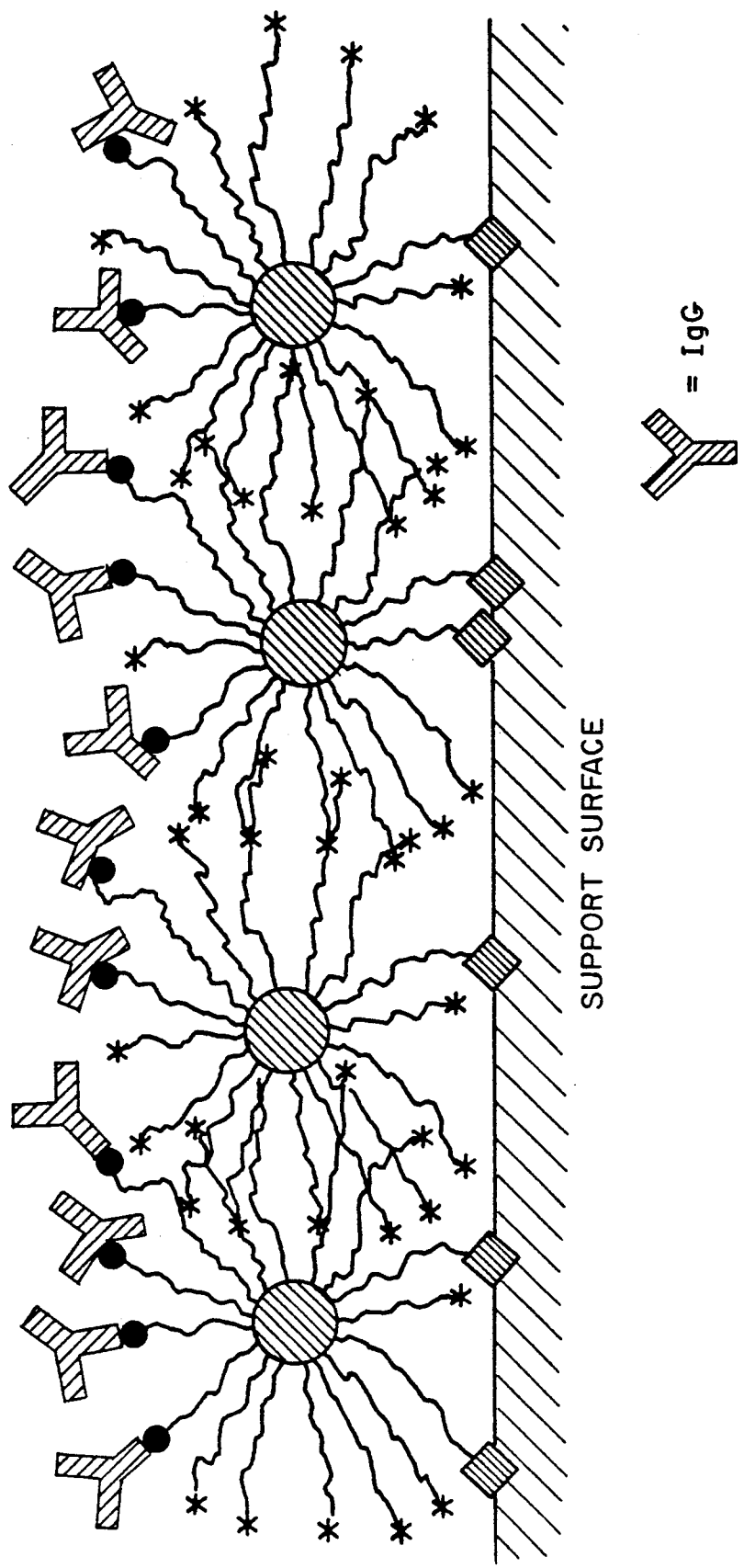
FIG. 4 illustrates the attachment of a biopolymer (IgG) to the surface of immobilized PEO star molecules.

The PEO star molecules can be covalently bonded onto an appropriate support surface using the methods previously described to thereby protect or "mask" the support from recognition by biopolymers. A dense monolayer coating of PEO star molecules can be accomplished by allowing contact between a solution or above pH 10 of activated (e.g. by tresyl) PEO star molecules and a surface containing, for example, amino or thiol groups in close proximity, such that the star molecules pack closely together, each attached by one or more arms to the surface at the site of the amino or thiol group. The remaining arms are available for attaching biopolymers or affinity ligands. The PEO-coated support surface can then be exposed to a biopolymer having amino or thiol groups which can couple to available tresylated hydroxyl groups. These available groups function as molecular leashes or tethers for the biopolymer. For example, anti-Protein C antibody can be attached to the star molecules and will be selective for its antigen, Protein C. The PEO monolayer prevents adsorption of the biopolymers onto the support surface and can thereby reduce or eliminate non-specific binding of undesired biopolymers. FIG. 4 demonstrates the use of star molecules for attaching affinity ligands, such as Immunoglobulin G. The symbol ◆ represents a covalent linkage between a PEO arm and an amino group on the support; ● represents a covalent linkage between a PEO arm and an amino or thiol group on IgG; ★ represents an endcapped previously tresylated hydroxyl (e.g., by treatment with mercaptoethanol).

A support surface can be aminated by ammonia plasma. The pH of a ten percent tresylated PEO star solution is adjusted to about ten or greater. The solution is then contacted with the surface for about fifteen minutes. Immediately after removing the support from the solution, the non-bound PEO star molecules are rinsed off with water. The support surface with the bound PEO stars are then contacted at once with the intended biopolymer. The biopolymer can be heparin, IgG, oligopeptides, etc. After a period of time, which can be from about two to about sixty minutes depending upon the biopolymer, the support surface is rinsed to remove and recover any unbound biopolymers. For the biopolymer to attach to the support surface, one out of f arms of the star needs to be covalently connected to the surface and another star arm out of f−1 needs to be covalently connected to the biopolymer.

Alternatively, it is possible to prepare star PEO molecules with a group other than a hydroxyl, such as an amino group (—NH₂), or a benzyl bromide group (—C₆H₄CH₂Br). A PEO chain having a sodium alkoxide (—ONa) end group is reacted with N-(2-bromoethyl)phthalimide:

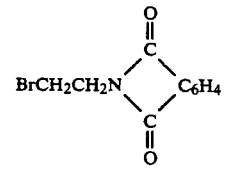

to form to a PEO phthalimide:

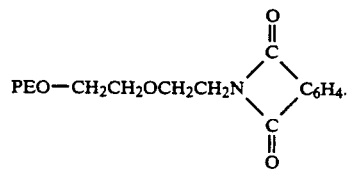

The PEO phthalimide then undergoes hydrolysis by acidified water to form PEO—CH₂CH₂OCH₂CH₂NH₂ while releasing phthalic acid. Another method includes reacting a hydroxy terminated PEO with a dibenzyl halide, such as BrCH₂—C₆H₄—CH₂Br to form a PEO chain with PEO—CH₂CH₂OCH₂—C₆H₄—CH₂Br. The benzyl bromide is then reacted with ammonia in methanol to create benzylamine at the end of the PEO. A PEO star molecule which is terminated by amino groups can be attached to a surface containing epoxy groups by direct reaction. Alternatively, the groups can be attached to a surface containing additional amino groups or to biopolymers having amino groups by a dialdelhyde, e.g. glutaraldehyde, followed by reduction of the imine (Schiff base) by sodium borohydride.

Due to the number of available PEO arms which can accommodate ligands, the hydrogels of this invention can be used to continuously separate, purify and concentrate therapeutic proteins. Processing of the proteins will require cycles of coupling and decoupling of the ligate to affinity ligands bound to the stars.

The affinity surface can be of any geometric shape, such as particles packed in beds, freely moving particles and porous membranes. Silica particles can be coated with PEO stars. In this case, polyethylene oxide is physically adsorbed to the silica surface but cannot be covalently bound unless the surface of the silica has been previously modified. Radiation can be used to cross-link physically adsorbed PEO star molecules to each other and in addition to silica surfaces which have been modified by vinyl silane. Thereby, the polyethylene oxide stars forms a shell covering the particle. The PEO star molecules can also be deposited into pores of ultrahigh molecular weight polyethylene such as Porex ™ (Auburn, Ga.), on the surface of Goretex ™ e-PTFE (expanded polytetrafluoroethylene) and Mylar ™ film.

As explained above, an immobilized layer of PEO star molecules on a support may have been formed by first creating reactive ends (e.g. tresyl) on the PEO star arms, which react with a specific group in the surface to form a covalent bond. This will leave numerous other reactive ends on the bound star molecules available to react with and bind affinity ligands. Alternatively, the immobilized layer of PEO star molecules may have been formed by radiation cross-linking.

In the latter case, once a PEO star molecule layer is affixed on the support surface, the terminal hydroxyl groups of the PEO arms are activated by tresylation or by other reaction previously described. The activated PEO star molecules in the immobilized layer are then exposed to the affinity ligand under conditions that favor covalent binding, for example pH 10 or above if the affinity ligand contains amino group. Examples of preferred ligands include, but are not limited to antibodies and $F_{ab}$ fragments thereof, Protein A, active polysaccharides, heparin-$NH_2$, anti-Protein C IgG, and the $F_{ab}$ fragment of anti-Protein C IgG.

Following affinity bonding of a specific ligate to its bound ligand, the PEO star-coated affinity support is washed to remove unbound proteins. Remaining bound proteins are then decoupled by changing the composition of the eluting buffer, for example by changing the ionic strength or the pH (e.g., to pH 10 or above) of the eluting buffer. For example, a 1M NaCl decoupling solution can be used in the case of anti-thrombin III bound to heparin. The decoupling results in free ligate in the eluting buffer. The ligate can then be separated from the eluting buffer using known techniques, such as by diafiltration described by Herak et al., *Biotech. Prog.* 5:9–17 (1989). Separated ligates can then be concentrated using known techniques. Examples of some specific ligates include but are not limited to macromolecules, monoclonal antibodies, antigens, proteins, peptides, viruses and cells (e.g., blood platelets, white blood cells, endothelial cells and other non-blood cells).

In addition to bioseparations, the hydrogels made according to this invention are useful for a variety of biomedical applications, due to their non-thrombogenic properties and excellent mechanical durability. They are suitable for in vivo applications in which blood contact is required, including blood contacting implantable vascular prostheses, angioplastic stents, cardiovascular sutures, metabolic support catheters, angioplastic balloon catheters, artificial hearts and ventricular assist devices. The hydrogels may also be used for ex vivo devices, such as hemodialysis membranes and membranes for extra-corporeal oxygenators.

A preferred application for the star molecules of this invention is in the manufacture of contact lenses. PEO star molecules can be grafted onto a suitable art recognized contact lens material, such as gas permeable lenses, using the techniques described herein. For example, the contact lens material can be immersed in a PEO star molecule solution and exposed to ionizing radiation to thereby graft the star molecules onto the contact lens surface. Alternatively, the surface of the contact lens materials can be modified by creating amino or thiol groups on it surface. The modified lens material is then exposed to activated PEO star molecules, such as tresylated star molecules described above. Due to the properties of the star molecules, absorption of proteineous deposits from natural enzymatic secretions of the eye by the star molecule coated-contact lens material can be eliminated or substantially reduced. Thus, the coated lenses will not become clouded or opaque because of lowered protein absorption.

Additional chemical components can be incorporated into the PEO star layers depending upon the application. In some instances it may be advantageous to incorporate heparin to further reduce thromogenicity. While heparin can be attached covalently to tresylated hydroxyls on the star molecules, it is also readily incorporated at high concentrations in hydrogel layers which are formed by simply adding it to the solution of the PEO stars before irradiation. In this form it elutes into the blood flow over a significant period of time.

The invention will be further illustrated by the following non-limiting Examples:

EXAMPLE 1

Synthesis and Characterization of Various PEO Hydrogels

Linear PEO and various forms of star molecules having the physical properties described below were electron beam irradiated, at a dose rate of about 0.1 megarads per second, and with a two megarad dose per pass under the beam to form unsupported hydrogels, in order better to study swelling phenomena. However, in practice the PEO solutions would be simultaneously cross-linked and covalently bonded to support surfaces by radiation. Radiation was delivered from a 3 MeV Van de Graaff generator (MIT High Voltage Research Laboratory).

Table 1 presents the apparent swelling ratio q at 25° C. (q=volume of hydrogel equilibrated in water/volume of original mixture irradiated) as a function of radiation dose D in megarad, and as a function of the star type. Two liner PEO samples are included for reference. The concentration of the solution as irradiated in every case was 10.0 wt/vol. % in MilliQ ® water (Millipore Corp., Bedford, Mass.). From Table 1 it is apparent that the swelling ratio q of hydrogels formed from star molecules is significantly less than for hydrogels from linear PEO types. Furthermore, the high styrene content Type II hydrogels (3103, 3229) exhibit virtually no swelling.

TABLE 1

Swelling Ratios g of 10 wt/vol. % Polymer/Water After Electron Beam Irradiation

| Linear PEO | D | q | [OH] µM |
| --- | --- | --- | --- |
| Nominal 300,000 M.W. | 4 | 2.03 | 0.33 |
|  | 6 | 1.92 | 0.35 |
| Nominal 100,000 M.W. | 4 | 2.8 | 0.71 |

TABLE 1-continued

Swelling Ratios g of 10 wt/vol. % Polymer/Water After Electron Beam Irradiation

| | | | | 6 | 2.4 | 0.83 |
|---|---|---|---|---|---|---|

Type I Stars (no styrene)

| | M.W. Total | # Arms | $M_{PEO}$ | D | q | [OH] µM |
|---|---|---|---|---|---|---|
| 3098 | 229,000 | 43 | 5,300 | 4 | 1.3 | 14.6 |
| 3210 | 142,000 | 40 | 3,460 | 4 | 1.4 | 20.0 |
| 3224 | 79,000 | 8 | 10,000 | 6 | 1.6 | 6.3 |

Type II Stars

| | M.W. Total | % S | # Arms | $M_{PEO}$ | $M_{PS}$ | D | q | [OH] µM |
|---|---|---|---|---|---|---|---|---|
| 3103 | 190,000 | 20 | 16 | 8,000 | 2,000 | 4 | ~1.0 | 8.4 |
| 3229 | 257,000 | 30 | 25 | 6,800 | 3,200 | 4 | ~1.0 | 9.6 |
| 3385 | 371,000 | 2 | 30 | 12,000 | 520 | 4 | 1.7 | 4.7 |
| | | | | | | 6 | 1.6 | 5.7 |

D: dose in megarads.
q: Swelling Ratio.
[OH]: gram equivalent per liter of gel swollen to equilibrium in water at 25° C.
Total M.W. of stars by light scattering.

From the results, the random cross-linking of star molecules cannot be expected to lead to networks like those produced from randomly cross-linked linear macromolecules, in which the functionality of the junction φ is necessarily four. In contrast, the incorporation of stars implies incorporation of junctions of high functionality φ, i.e., φ=number of arms. Further, the "junction" is in effect a high modulus poly DVB core, in Type I stars, and an even more complicated entity, i.e., poly DVB with short polystyrene arms, in Type II stars. Thus, the space occupied by the "junction", and the thermodynamically adverse junction-water interaction place the star hydrogel beyond the tenets of the Flory-Huggins theory of swelling of randomly cross-linked networks.

The last column in Table 1 shows the molar hydroxyl content of the gel at equilibrium in water [OH], calculated as: (mols OH/100 g. dry polymer)$q^{-1}$, wherein the first term is determined as (number of arms/total M.W.).100. Each original solution at 10 wt/vol. % contains 100 grams of dry polymer per liter. The final wt/vol. % polymer in the gel at equilibrium with water is thus 10/q. This is very important if the star hydrogel is to be deployed as a model biomaterial to which bioactive species are to be grafted. It is desirable to have a high value of [OH] and a low swelling ratio q in order that the biomaterial remain approximately in the shape in which it was cast. This is especially important for the case that the hydrogel has been formed on a support which is incapable of swelling or shrinking. Stars 3098 and 3210 as hydrogels provide examples.

In the hydrated state, i.e., in equilibrium with blood plasma, preliminary studies of platelet deposition indicate that the surface of star hydrogel is entirely PEO, that is, the poly DVB core is buried and inaccessible, because of the fact that the star hydrogel acts as if it were a hydrogel of linear PEO. Cross-linking of these arms is random, granting that all PEO arms have approximately the same molecular weight on a given star type as a consequence of the anionic polymerization route. Under an electron beam, hydroxyl radicals created from water constitute the principal reagent and therefore, the PEO rather than the poly DVB and PS experiences macroradical formation and subsequent coupling. To some degree scission of the arms must occur competitively with cross-linking under radiation.

The terminal, hydroxyl concentrations [OH] calculated in Table 2 do not take this into account.

Biocompatibility

Hydrogels containing Type I Stars 3098 (no polystyrene content) or Type II Stars 3385 (2% polystyrene, 98% PEO), described above, were examined for biocompatibility.

Tubular specimens of hydrogel were prepared from 10 wt/vol. % solutions of star polymers 3098 and 3385 using 0.7 ml of solution centrifugally cast and irradiated under six megarads inside glass tubes of 10 cm length×9 mm lumen. These were tested in an ex vivo shunt model (indium 111 labeled platelets, baboon) with uncoated glass tubes as control. Over a period of one hour at a blood flow rate of 100 ml/min., there was no increase of indium count above background for the two hydrogel surfaces, whereas in glass control tubes (no coating) the count more than trebled over background.

Using similar techniques, glass tubes lined with 0.7 ml hydrogels formed from 10 wt./vol. % solutions of linear PEO of 100,000 and 300,000 M.W., respectively, under the same does were prepared. Upon equilibration at 25° C. with pure water, the apparent swelling ratios (final volume:initial volume) were 1.3, 1.3, 2.8 and 2.0 for Star 3098, Star 3385, PEO 100,000 and PEO 300,000 hydrogels, respectively. Values of 1.3, as compared to two or more, mean that the star polymer based hydrogels when exposed to blood do not expand to such a degree as to compromise attachment to the surface on which they were cast. The lack of platelet uptake indicates that the star polymers in hydrogel form present a "pure" PEO surface to blood. As such, the DVB cores were shielded from access of plasma proteins by the PEO arms.

EXAMPLE 2

Synthesis of PEO Star Molecule Coated Contact Lenses

A series of gas permeable contact lenses were coated with PEO star molecules. The lenses were type RXD manufactured by Polymer Technology Corporation and were ground to the correct shape from cylindrical wafers which were cut from rods. The rods were made by polymerization of perfluoroacrylates and methacrylates, and had high oxygen permeability. The lenses were considered to be rigid.

The convex and then the concave side of the lenses were exposed to Plasma Enhanced Chemical Vapor Deposition (PECVD) in a Plasmatherm ® Dual Chamber device, under the following conditions: five minute time exposure, 100 watts at 13.56 MHz and 104 DC volts. Ammonia gas was flowed through the chamber at 20 standard cubic centimeters per minute at a pressure of 500 millitorr and a temperature of 30° C.

Following this treatment, the lenses were analyzed by X-ray Photoelectron Spectroscopy (XPS), also called ESCA. The control lenses had zero atom percent nitrogen, and the treated lenses had an average of about five atomic percent nitrogen which was presumably in the form of amino groups.

PEO star molecule 3509 (number assigned by P. Rempp) had the following characteristics as reported by Rempp:

1. Weight average molecular weight $M_w$: 576,000;

2. Molecular weight of PEO arm as calculated from ratio of ethylene oxide to potassium naphthenide. $M_{arm} = 10,000$; and
3. Deduced number of arms per star $f_w = 57.6$, thus the weight average number of hydroxyls per molecule is also 57.6.

Following the procedure recommended by Nilsson et al., *Methods in Enzymology*. Vol. 104, p 55 (Academic Press 1984), 1.0 gram of the star material was dissolved in 15 grams dichloromethane (dry) at $-10°$ C. 100 µl triethyl amine and then 73 µl trifluoroethane sulfonyl ("tresyl") chloride ($CF_3CH_2SO_2Cl$) were added to the dichloromethane solution. The dichloromethane and triethylamine had been dehydrated by storage over molecular sieves.

The reaction was allowed to proceed for 90 minutes as the temperature rose from $-10°$ C. to $+20°$ C. The polymer was then precipitated when cold anhydrous methanol was added. The precipitate was centrifuged to form a pellet, rewashed twice with cold methanol, and then dried under vacuum at 25° C. Elemental analysis for sulfur showed greater than 80% tresylation of the original hydroxyls.

The ammonia plasma treated lenses (APTL lenses) were coated by the activated star molecules which were accomplished by contacting each lens with 1 ml of a tris buffer (pH 10) containing 100 mg of tresylated stars (PEO 3509) at room temperature. The stars remained in the solution for 60 minutes.

The lenses were then repeatedly rinsed with MilliQ® water. Following drying, the lenses were analyzed again by XPS. Significant nitrogen was found in the surface, ca. 2.5 atomic percent. This is consistent with the presumed thickness of the attached PEO star layer. It was determined by intrinsic viscosity that the average PEO star molecule has a diameter (as an "Einstein" model sphere) of 250 angstroms (25 nm). With the assumption that each star molecule occupies a circular area of the same diameter, the removal of water from this "tethered" spherical molecule will result in its collapse to a thickness on the order of 12 angstroms (1.2 nm) which was sufficiently thin to allow XPS radiation to probe the contact lens substance under this layer. The coating had in fact resulted which was proved by attempting rewetting with water of ammonia plasma treated lenses (APTL). The same occurred after exposure to the tresylated PEO stars.

The APTL lenses permitted the water to "bead up," i.e., water did not form a continuous layer, whereas, by contrast the APTL with PEO attached allowed water to form a continuous film on both convex and concave surfaces. Several drying and rewetting steps were carried out with the same result, indicating that the PEO stars were covalently attached.

Equivalents

Those skilled in the art will recognize, or be able to ascertain, using no more than routine experimentation, many equivalents to the specific embodiments of the invention described herein. Such equivalents are intended to be encompassed by the following claims.

I claim:

1. A method for immobilizing polyethylene oxide (PEO) star molecules to a support surface to form a layer thereon, comprising the steps of:
    a) exposing an organic solution, comprising polyethylene oxide star molecules each of which consists essentially of a plurality of hydroxy-terminated polyethylene oxide chains attached to a divinyl benzene core, to a reagent to affix reagent groups to the hydroxy termini, said reagent groups permitting subsequent attachment of amino or thiol groups to the PEO chain ends by displacement, thereby forming activated polyethylene oxide star molecules with active reagent end groups;
    b) separating the activated polyethylene oxide star molecules with active reagent end groups from the organic solvent;
    c) dissolving the activated polyethylene oxide star molecules in an aqueous solution; and
    d) contacting the solution of step (c) with a support surface containing amino and/or thiol groups to covalently bind the reagent terminated star molecules, thereby immobilizing the reagent terminated star molecules in a dense layer to the support surface.

2. The method of claim 1, wherein the support surface is selected from the group consisting of particles, porous polymeric membranes, polymeric film, and biomedical devices.

3. The method of claim 1, wherein the support surface is selected from the group consisting of blood contacting vascular prostheses, angioplastic stents, cardiovascular suture, metabolic support catheters, angioplastic balloon catheters, artificial hearts, ventricular assist devices, hemodialysis membranes and membranes for extracorporeal oxygenators.

4. The method of claim 1, wherein the reagent is selected from the group consisting of tresyl chloride, tosyl chloride, mesyl chloride, epichlorhydrin, cyanuric chloride, carbonyl diimidazole and a mixture of succinic anhydride and succinimide.

5. A product produced by the method of claim 1.

6. The method of claim 1, further comprising the steps of:
    e) washing the support surface to remove any non-bound star molecules, leaving the activated polyethylene oxide star molecules remaining bound thereto; and
    f) contacting the support surface after step (e) with an affinity ligand having amino and/or thiol groups thereon, to covalently bind the ligand to the activated polyethylene oxide chains.

7. The method of claim 6, wherein the affinity ligand is selected from the group consisting of antibodies, Protein A, $F_{ab}$ fragments of antibodies and active polysaccharides.

8. The method of claim 7, wherein the active polysaccharide is heparin.

9. A method of separating and purifying a ligate, comprising the steps of:
    a) providing a support surface having coated thereon, a layer comprising polyethylene oxide star molecules having a plurality of ligand-terminated polyethylene oxide chains attached to a divinyl benzene core;
    b) contacting a sample containing a ligate under conditions sufficient to bind the ligate to the ligand;
    c) removing any unbound ligates from the PEO star layer surface;
    d) adjusting ionic strength and/or pH of the sample to thereby remove the bound ligate from the PEO star layer; and
    e) collecting the bound ligates.

10. The method of claim 9, wherein the support surface is selected from the group consisting of silica particles, porous polymeric material, polymeric film and ultrahigh molecular weight high density polyethylene.

11. The method of claim 10, wherein the ligate is selected from the group consisting of macromolecules, monoclonal antibodies, antigens, viruses and cells.

12. The method of claim 11, wherein the cells are selected from the group consisting of blood platelets, white blood cells and endothelial cells.

13. The method of claim 9, wherein the ligand is selected from the group consisting of antibodies, Protein A, $F_{ab}$ fragments of antibodies, and active polysaccharides.

14. The method of claim 13, wherein the active polysaccharide is heparin.

15. The method of claim 13, wherein the ligand is a monoclonal anti-Protein C IgG or Fab fragment thereof.

16. A biocompatible, non-thrombogenic layer, comprising immobilized polyethylene star molecules having a plurality of hydroxy-terminated polyethylene oxide chains attached to a polymeric core.

17. The layer of claim 16, wherein the star molecules comprise from about six to about two hundred hydroxy-terminated polyethylene oxide chains attached to a polymeric core that is divinyl benzene, wherein each chain has a molecular weight range of from about 1,000 to about 10,000 atomic mass units (a.m.u.).

18. A contact lens having a covalently linked surface layer of immobilized polyethylene oxide star molecules having a plurality of hydroxy-terminated polyethylene oxide chains attached to a polymeric core.

19. A contact lens of claim 18, wherein the polymeric core of the PEO star molecule is divinyl benzene and each chain of the star molecule has a molecular weight from about 1,000 to about 10,000.

20. A contact lens made by the method of claim 1.

* * * * *